(12) United States Patent
Liang

(10) Patent No.: US 11,857,730 B2
(45) Date of Patent: Jan. 2, 2024

(54) EYESHADE AND ELECTROENCEPHALOGRAM DETECTION SYSTEM

(71) Applicant: BOE TECHNOLOGY GROUP CO., LTD., Beijing (CN)

(72) Inventor: Siyang Liang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 639 days.

(21) Appl. No.: 16/923,921

(22) Filed: Jul. 8, 2020

(65) Prior Publication Data

US 2021/0008334 A1 Jan. 14, 2021

(30) Foreign Application Priority Data

Jul. 8, 2019 (CN) .......................... 201921055266.0

(51) Int. Cl.
*A61M 21/02* (2006.01)
*A61B 5/00* (2006.01)
*A61B 5/369* (2021.01)

(52) U.S. Cl.
CPC .............. *A61M 21/02* (2013.01); *A61B 5/369* (2021.01); *A61B 5/6803* (2013.01)

(58) Field of Classification Search
CPC .......... A61M 21/02; A61M 2021/0066; A61M 2205/3569; A61M 2205/3584;
(Continued)

(56) References Cited

U.S. PATENT DOCUMENTS

2014/0303428 A1* 10/2014 Berka .................. A61B 5/6803
600/27
2015/0190607 A1* 7/2015 Sugio ........................ A61F 9/04
600/27
(Continued)

FOREIGN PATENT DOCUMENTS

CN 204890332 U 12/2015
CN 106974650 A 7/2017
(Continued)

OTHER PUBLICATIONS

English Translation of CN110251306A, Ni, Yu et al, Sep. 20, 2019 (see attached) (Year: 2019).*

*Primary Examiner* — Sunita Reddy
(74) *Attorney, Agent, or Firm* — Nath, Goldberg & Meyer; Joshua B. Goldberg

(57) ABSTRACT

An eyeshade and an electroencephalogram detection system are provided. The eyeshade includes an eyeshade main body; and an electroencephalogram acquisition unit, a controller and a heating unit which are disposed on the eyeshade main body. The electroencephalogram acquisition unit is configured to acquire a brain electrical signal of a wearer. The controller includes a converter and is configured to receive the brain electrical signal from the electroencephalogram acquisition unit, the converter is detachably coupled to the electroencephalogram acquisition unit and is configured to convert the brain electrical signal into a communication signal and transmit the communication signal to outside when coupled to the electroencephalogram acquisition unit. The heating unit is configured to heat an eye region of the wearer.

17 Claims, 2 Drawing Sheets

(58) Field of Classification Search
CPC .... A61M 2205/3592; A61M 2205/505; A61M 2210/0612; A61M 2230/10; A61B 5/369; A61B 5/6803; A61B 5/015; A61B 5/4815; A61B 5/4836; A61B 2560/0252; A61B 5/256; A61B 5/291
USPC .................................................. 600/26–28
See application file for complete search history.

(56) References Cited

U.S. PATENT DOCUMENTS

| | | | | |
|---|---|---|---|---|
| 2016/0193442 | A1* | 7/2016 | Adamczyk | A61M 21/02 |
| | | | | 600/27 |
| 2017/0020454 | A1* | 1/2017 | Keteyian | G16H 40/67 |
| 2018/0103917 | A1* | 4/2018 | Kim | A61B 5/291 |
| 2019/0200925 | A1* | 7/2019 | Aimone | A61B 5/6831 |

FOREIGN PATENT DOCUMENTS

| | | | |
|---|---|---|---|
| CN | 207666587 U | 7/2018 | |
| GB | 2600680 A * | 5/2022 | ......... A41D 13/0012 |

\* cited by examiner

EYESHADE AND ELECTROENCEPHALOGRAM DETECTION SYSTEM

CROSS-REFERENCE TO RELATED APPLICATION

The present application claims priority from Chinese patent application No. 201921055266.0 filed on Jul. 8, 2019, the content of which is incorporated herein in its entirety by reference.

TECHNICAL FIELD

The present disclosure relates to the field of wearable equipment technologies, and in particular, to an eyeshade and an electroencephalogram detection system.

BACKGROUND

The eyeshade can be used for shading light and eliminating interference, and is widely applied to sleep aids or eye massage.

SUMMARY

Embodiments of the present disclosure provide an eyeshade and an electroencephalogram detection system.

A first aspect of the present disclosure provides an eyeshade, including:
an eyeshade main body; and
an electroencephalogram acquisition unit, a controller and a heating unit which are disposed on the eyeshade main body,
wherein the electroencephalogram acquisition unit is configured to acquire a brain electrical signal of a wearer;
the controller includes a converter and is configured to receive the brain electrical signal from the electroencephalogram acquisition unit, the converter is detachably coupled to the electroencephalogram acquisition unit and is configured to convert the brain electrical signal into a communication signal and transmit the communication signal to outside when coupled to the electroencephalogram acquisition unit; and
the heating unit is configured to heat an eye region of the wearer.

In some embodiments, the controller further includes a temperature controller coupled to the heating unit and configured to adjust a heating temperature of the heating unit.

In some embodiments, the wearer provides a control instruction to the temperature controller, and the temperature controller adjusts the heating temperature of the heating unit according to the control instruction.

In some embodiments, the controller further includes a processor coupled to the temperature controller and the electroencephalogram acquisition unit and configured to generate a control signal according to the brain electrical signal acquired by the electroencephalogram acquisition unit, and the temperature controller is configured to adjust the heating temperature of the heating unit according to the control signal.

In some embodiments, the controller further includes a first coupling structure which is electrically conductive, the electroencephalogram acquisition unit includes a second coupling structure which is electrically conductive, and the electroencephalogram acquisition unit is detachably coupled to the first coupling structure of the controller by the second coupling structure; and
when the second coupling structure is coupled to the first coupling structure, the electroencephalogram acquisition unit is electrically coupled to the converter, and the brain electrical signal is transmitted from the electroencephalogram acquisition unit to the converter.

In some embodiments, the first coupling structure includes a data interface and the second coupling structure includes a data interface that matches with the data interface of the first coupling structure, the electroencephalogram acquisition unit is detachably coupled to the controller through the data interface of the first coupling structure and the data interface of the second coupling structure, and the controller receives the brain electrical signal from the second coupling structure through the data interface of the first coupling structure.

In some embodiments, the converter includes an analog-to-digital conversion circuit which converts the brain electrical signal being an analog signal into a digital brain electrical signal, and a wireless transmission circuit which transmits the digital brain electrical signal to an upper computer.

In some embodiments, the analog-to-digital conversion circuit includes an analog-to-digital converter, and the wireless transmission circuit includes a bluetooth module, a Wi-Fi module, or a Zigbee module.

In some embodiments, the electroencephalogram acquisition unit includes a flexible circuit board and an electrode disposed on the flexible circuit board; and
the controller is disposed on an outer side of the eyeshade main body, an opening is provided in a portion of the eyeshade main body that overlaps with a forehead of the wearer when the eyeshade is worn by the wearer, the flexible circuit board is detachably coupled to the controller, and the flexible circuit board is capable of passing through the opening.

In some embodiments, the electrode includes a plurality of sub-electrodes including differential electrodes and a reference electrode; and
a differential signal receiving port of the controller is configured to receive a signal acquired by the differential electrodes, and a reference voltage receiving port of the controller is configured to receive a signal acquired by the reference electrode.

In some embodiments, the differential electrodes and the reference electrode are arranged in a direction parallel to a length of the flexible circuit board, and the differential electrodes include first and second differential electrodes respectively located on both sides of the reference electrode.

In some embodiments, an adhesive unit is provided on a side of the flexible circuit board distal to the electrodes and/or on both ends of the eyeshade main body.

In some embodiments, a fixing member which is electrically conductive is disposed on an outer side of the eyeshade main body, the controller is fixed to the eyeshade main body through the fixing member, and the temperature controller is electrically coupled to the heating unit through the fixing member.

In some embodiments, the fixing member includes a magnetic clasp.

In some embodiments, a light-shielding layer is disposed on an inner side of the eyeshade main body, and recesses are provided in a portion of the light-shielding layer that overlaps with the eye region of the wearer when the eyeshade is worn by the wearer.

In some embodiments, the heating unit is disposed within the light-shielding layer.

In some embodiments, the heating unit includes a material of graphene.

In some embodiments, the controller is in wireless communication with the electroencephalogram acquisition unit.

In some embodiments, the heating unit is disposed on an inner side of the eyeshade main body and overlaps with the eye region of the wearer when the eyeshade is worn by the wearer.

A second aspect of the present disclosure provides an electroencephalogram detection system, including the eyeshade of any one of the embodiments of the first aspect of the present disclosure and an upper computer, and the upper computer is configured to receive the communication signal transmitted from the converter and to evaluate a degree of relaxation or tension of the brain of the wearer according to the communication signal.

BRIEF DESCRIPTION OF THE DRAWINGS

Embodiments of the present disclosure will be more clearly understood from the following detailed description in conjunction with accompanying drawings, in which.

DETAILED DESCRIPTION

Exemplary embodiments of the present disclosure will be described in detail below with reference to the accompanying drawings. It should be understood that the exemplary embodiments described herein are only adopted to illustrate and explain the present disclosure, and are not intended to limit the present disclosure.

Electroencephalogram detection is one of methods for detecting function of human nervous system. By placing electrodes on the scalp, detecting a continuous rhythm potential change (that is, a brain electrical signal) in the activity of human brain nerve cells, and transmitting the brain electrical signal to an electroencephalograph for processing, a waveform of the potential change produced by the activity of human brain nerve cells can be recorded to generate an electroencephalogram. The brain electrical signals acquired at different positions of a human head can reflect respective states of human. The brain electrical signal near the forehead of human can reflect a concentration degree and a relaxation degree of the brain, and is generally used for detecting sleep depth of human.

Figure 1:
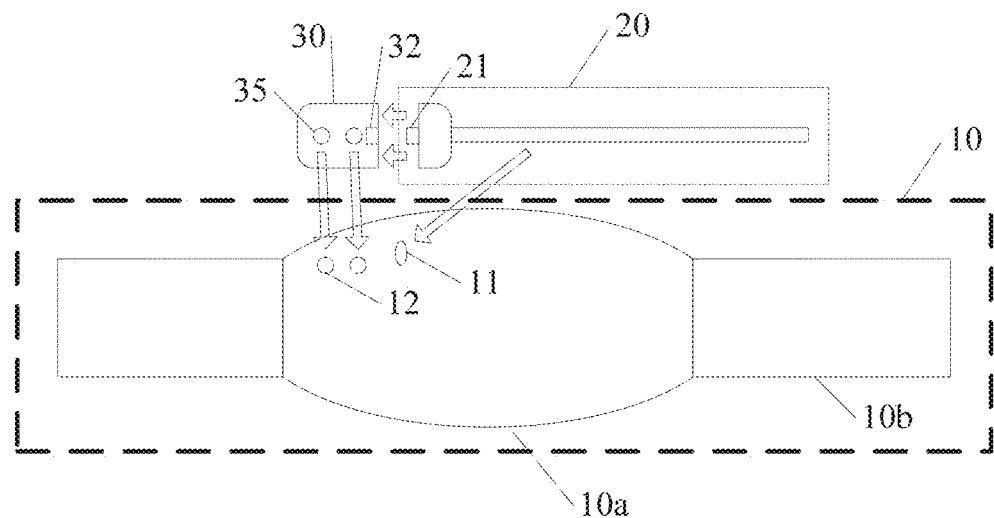
FIG. 1 is a schematic exploded structural diagram of an eyeshade according to an embodiment of the present disclosure.
Figure 2:
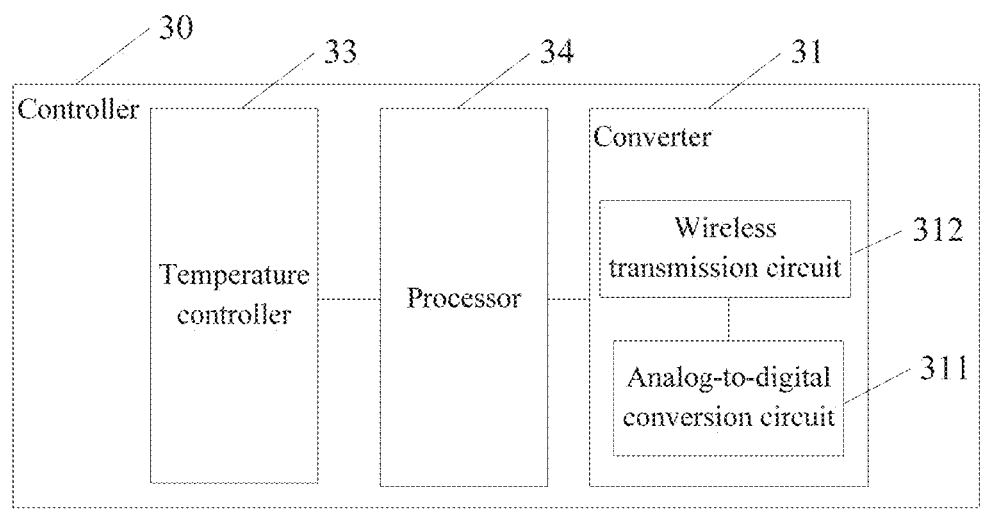
FIG. 2 is a schematic structural diagram of a controller according to an embodiment of the present disclosure.

An embodiment of the present disclosure provides an eyeshade. FIG. 1 is a schematic exploded structural diagram of an eyeshade according to an embodiment of the present disclosure, and FIG. 2 is a schematic structural diagram of a controller according to an embodiment of the present disclosure. As shown in FIGS. 1 and 2, the eyeshade includes an eyeshade main body 10, and an electroencephalogram acquisition unit 20, a controller 30, and a heating unit 40 (see FIG. 4) which are disposed on the eyeshade main body 10.

The electroencephalogram acquisition unit 20 is configured to acquire a brain electrical signal of a wearer.

The controller 30 includes a converter 31 and is configured to receive the brain electrical signal from the electroencephalogram acquisition unit 20, and the converter 31 is detachably coupled to the electroencephalogram acquisition unit 20 and is configured to convert the brain electrical signal into a communication signal and transmit the communication signal to outside when the converter 31 is coupled to the electroencephalogram acquisition unit 20. For example, the converter 31 of the controller 30 may transmit the communication signal to a server (e.g., a computer, a mainframe computer, or the like) for storage, processing, and/or display, or may transmit the communication signal to a terminal (e.g., a personal digital assistant, a mobile phone, a notebook computer, a personal computers, or the like) for storage, processing and/or display. In some embodiments, the converter 31 may transmit the communication signal to an upper computer, so that the upper computer may evaluate a degree of relaxation of the brain and/or a degree of stress of the brain of the wearer according to the communication signal. In some embodiments, the controller 30 receives the brain electrical signal from the electroencephalogram acquisition unit 20 through the converter 31. The upper computer may be a device which receives the communication signal from the converter 31 in a wired or wireless communication manner and evaluates the degree(s) of relaxation and/or stress of the brain of the wearer according to the communication signal. For example, the upper computer may be a Personal Digital Assistant (PDA), a mobile phone, a laptop computer, a personal computer, a server, and the like. For example, modern scientific researches have shown that frequencies of brain waves includes at least the following four frequency ranges: 1 Hz to 3 Hz (a brain wave having a frequency within this range is referred to as a δ wave), 4 Hz to 7 Hz (a brain wave having a frequency within this range is referred to as a θ wave), 8 Hz to 13 Hz (a brain wave having a frequency within this range is referred to as an α waves), and 14 Hz to 30 Hz (a brain wave having a frequency within this range is referred to as a β wave). In general (e.g., for an 18 year old or older person), the β wave may indicate an extreme fatigue state, a lethargy state, and/or an anesthesia state, the θ wave may indicate a frustrated state and/or a depression state, the α wave may indicate a happy state and/or a meditation state, and the 0 wave may indicate a mental tension state, an emotional agitation state, and/or a hyperactivity state. Therefore, the processor 34 of the controller 30 may extract a frequency of the current brain electrical signal collected by the electroencephalogram acquisition unit 20, and then determine a degree of relaxation or tension of the brain of the wearer according to the range to which the frequency belong. It should be understood that the present disclosure is not limited thereto. For example, with the deepening of scientists' understanding of brain waves, the frequencies of the brain waves may be divided into more frequency ranges than those described herein to reflect more mental states and/or physiological states of a person.

The heating unit 40 is configured to heat an eye region of the wearer. For example, the heating unit 40 may be a heater including a thermistor.

In an embodiment of the present disclosure, a side of the eyeshade main body 10 which is away from (or is distal to) the wearer when the wearer wears the eyeshade is referred to as an outer side of the eyeshade main body 10 (or may be referred to as a first interface of the eyeshade main body 10), and a side of the eyeshade main body 10 which faces (or is proximal to) the wearer when the wearer wears the eyeshade is referred to as an inner side of the eyeshade main body 10 (or may be referred to as a second interface of the eyeshade main body 10). In an embodiment of the present disclosure, a portion of the electroencephalogram acquisition unit 20 and the controller 30 are disposed on the outer side of the eyeshade main body 10.

In some embodiments, the converter 31 being detachably coupled to the electroencephalogram acquisition unit 20 means that the converter 31 and the electroencephalogram acquisition unit 20 may be temporarily integrated as a single component, and that the converter 31 may be separated from the electroencephalogram acquisition unit 20. When the converter 31 and the electroencephalogram acquisition unit 20 are temporarily formed as a single component, a signal may be transmitted between the converter 31 and the electroencephalogram acquisition unit 20. In some embodiments, as shown in FIG. 1, the controller 30 includes a first coupling structure 32 which is electrically conductive, the electroencephalogram acquisition unit 20 includes a second coupling structure 21 which is electrically conductive, and the electroencephalogram acquisition unit 20 is detachably coupled to the first coupling structure 32 of the controller 30 through the second coupling structure 21. When the electroencephalogram acquisition unit 20 is coupled to the first coupling structure 32 through the second coupling structure 21, the electroencephalogram acquisition unit 20 is electrically coupled to the converter 31, and the brain electrical signal acquired by the electroencephalogram acquisition unit 20 can be transmitted to the converter 31 of the controller 30.

The converter 31 may include an analog-to-digital conversion circuit 311 and a wireless transmission circuit 312. The analog-to-digital conversion circuit 311 converts the received brain electrical signal that is an analog signal into a digital brain electrical signal, and the wireless transmission circuit 312 transmits the digital brain electrical signal to the upper computer. The heating unit 40 is disposed on the inner side of the eyeshade main body 10, and overlaps with the eye region of the wearer when the eyeshade is worn by the wearer. The heating unit 40 is electrically coupled to the controller 30.

The analog-to-digital conversion circuit 311 may be implemented by an analog-to-digital converter (ADC), such as AD997A, AD574A, AD4003, AD4000, and the like.

The wireless transmission circuit 312 may be implemented by a bluetooth module, a Wi-Fi module, a Zigbee module, and the like. For example, the Bluetooth module may be CC2541, CC2640, SKB369, RF-BM-SOA, and the like; the Wi-Fi module may be CC3100 of Ti, MW300 of Marvell, BCM4390 of Broadcom, MT7688 of MTK, and the like; and the Zigbee module may be JN5169 of NXP CC2530 of Ti, and the like.

The eyeshade of the embodiment of the present disclosure includes the heating unit 40 and the electroencephalogram acquisition unit 20, and thus the brain electrical signal of the wearer can be acquired while heating the eye region of the wearer. In addition, the electroencephalogram acquisition unit 20 can be detached from the eyeshade, so that the wearer can detach the electroencephalogram acquisition unit 20 from the eyeshade when the brain electrical signal is not acquired, and the weight of the eyeshade is reduced.

In some embodiments, the first coupling structure 32 of the controller 30 includes a data interface including, but not limited to, a type-C interface or a micro-USB interface, and the second coupling structure 21 of the electroencephalogram acquisition unit 20 includes a data interface that matches with the data interface of the first coupling structure 32. In this case, the electroencephalogram acquisition unit 20 is detachably coupled to the controller 30 through the matched data interfaces, and the controller 30 may receive the brain electrical signal from the second coupling structure 21 of the electroencephalogram acquisition unit 20 through the data interface of the first coupling structure 32. When the wearer does not use the electroencephalogram acquisition unit 20 while using the eyeshade to heat the eye region, the electroencephalogram acquisition unit 20 can be removed to reduce the weight of the eyeshade.

In some embodiments, the controller 30 may communicate wirelessly (for example, via Bluetooth, Wi-Fi, and the like) with the electroencephalogram acquisition unit 20. In this case, wireless communication modules that can communicate wirelessly with each other are included in the controller 30 and the electroencephalogram acquisition unit 20, respectively.

The controller 30 may further include a temperature controller 33, and the temperature controller 33 is coupled to the heating unit 40 and is configured to adjust a heating temperature of the heating unit 40.

In some embodiments, the controller 30 may further include a processor 34, the processor 34 is coupled to the temperature controller 33 and the electroencephalogram acquisition unit 20 and is configured to generate a control signal according to the brain electrical signal acquired by the electroencephalogram acquisition unit 20, and the temperature controller 33 is configured to adjust the heating temperature of the heating unit 40 according to the control signal.

The temperature controller 33 and the processor 34 may be integrated in a single processing device, or may be implemented by different processing devices. The processing device(s) may be, for example, a central processing unit CPU (for example, ARM Cortex-M3), a digital signal processor DSP (for example, CEVA DSP), a micro control unit MCU (for example, STM32, MSP 430), and the like.

In some embodiments, a control instruction may be provided to the temperature controller 33 by the wearer, and the temperature controller 33 adjusts the heating temperature of the heating unit 40 according to the control instruction. In some embodiments, the control signal may be generated by the processor 34 according to the brain electrical signal acquired by the electroencephalogram acquisition unit 20, and the temperature controller 33 adjusts the heating temperature of the heating unit 40 according to the control signal, so as to achieve automatic adjustment of the temperature. By adjusting the heating temperature of the heating part 40, different temperatures can be achieved to heat the eye region of the wearer, and thus the brain electrical signals of the wearer at different heating temperatures can be detected to analyze the brain electrical activities of the wearer at different heating temperatures.

In some embodiments, providing the control instruction to the controller 30 by the wearer may include providing the control instruction through a button or a rotary knob or the like disposed on the controller 30, but is not limited thereto. In some embodiments, when the processor 34 adjusts the heating temperature of the heating unit 40 according to the brain electrical signal acquired by the electroencephalogram collection portion 20, the processor 34 obtains (for example, calculates or queries according to pre-stored information) a corresponding control signal according to the brain electrical signal acquired by the electroencephalogram collection portion 20, and the temperature controller 33 controls the heating temperature of the heating unit 40 according to the corresponding control signal, so as to adjust the heating temperature of the heating unit 40 in real time. In some embodiments, for example, when the wearer is in a relatively nervous state, the brain of the wearer is highly active, and the brain electrical signal varies greatly, the heating temperature of the heating unit 40 may be increased appropriately to relax the wearer, so that the wearer may enter into a sleep state more quickly. In some embodiments, the heating unit 40 may have a heating temperature up to about 42° C. to effectively relieve eye fatigue and promote local blood circulation.

Figure 3:
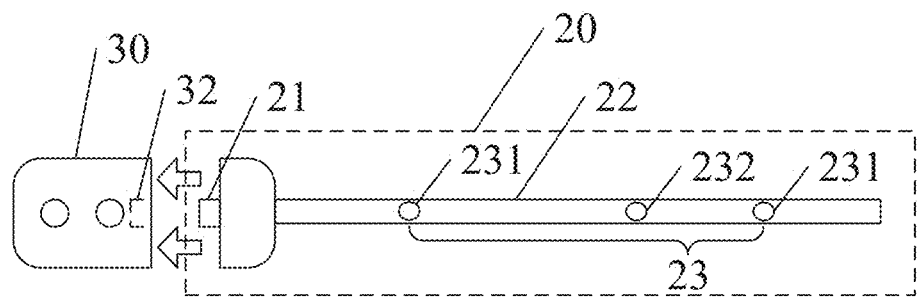
FIG. 3 is a schematic diagram of a electroencephalogram acquisition unit according to an embodiment of the present disclosure.

FIG. 3 is a schematic diagram of an electroencephalogram acquisition unit according to an embodiment of the present disclosure. As shown in FIG. 3, the electroencephalogram acquisition unit 20 includes a flexible circuit board 22 and an electrode 23 disposed on the flexible circuit board 22.

The controller 30 is disposed on the outer side of the eyeshade main body 10, and the flexible circuit board 22 is detachably coupled to the controller 30 through the first coupling structure 32 and the second coupling structure 21. As shown in FIGS. 1 and 3, an opening 11 is provided in a portion of the eyeshade main body 10 that overlaps with a forehead of the wearer when the eyeshade is worn by the wearer, and the flexible circuit board 22 may pass through the opening 11, so that the electrode 23 on the flexible circuit board 22 is in contact with the forehead of the wearer.

In some embodiments, the electrode 23 includes a plurality of sub-electrodes including differential electrodes 231 and a reference electrode 232. The controller 30 may include a differential signal receiving port and a reference voltage receiving port. The differential signal receiving port of the controller 30 is configured to receive a signal acquired by the differential electrodes 231, and the reference voltage receiving port of the controller 30 is configured to receive a signal acquired by the reference electrode 232.

In some embodiments, two differential electrodes 231 (which may be electrically coupled to the differential signal receiving port of the controller 30) and one reference electrode 232 (which may be electrically coupled to the reference voltage receiving port of the controller 30) are arranged in a direction parallel to a length of the flexible circuit board 22. The two differential electrodes 231 are respectively disposed on both sides of the reference electrode 232, and the brain electrical signal is transmitted to a corresponding signal receiving port of the controller 30 through the electrode 23.

In some embodiments, an adhesive unit 10c is provided on a side of the flexible circuit board 22 away from (i.e., distal to) the electrodes and/or on both ends of the eyeshade main body 10. For example, a portion of the adhesive unit 10c is disposed on the outer side of one end of the eyeshade main body 10 (as shown in the upper right corner of FIG. 4), and the other portion of the adhesive unit 10c is disposed on the inner side of the other end of the eyeshade main body 10 (as shown in the lower left corner of FIG. 4), so that the eyeshade main body 10 can be fixed to the head of the wearer by the adhesive units 10c. In some embodiments, the adhesive unit 10c includes a Velcro.

In some embodiments, a fixing member which is electrically conductive is disposed on the outer side of the eyeshade main body 10, the controller 30 is fixed to the eyeshade main body 10 by the fixing member, and the temperature controller 33 is electrically coupled to the heating unit 40 by the fixing member.

In some embodiments, the fixing member includes a magnetic clasp. In some embodiments, as shown in FIG. 1, the magnetic clasp includes a female clasp 12 disposed on the eyeshade main body 10 and a male clasp 35 disposed on the controller 30. The female clasp 12 is electrically coupled to the heating unit 40 through a wire inside the eyeshade main body 10. In the embodiment shown in FIG. 1, each of the number of female clasps 12 and the number of male clasps 35 is two (2). In some other embodiments, each of the number of female clasps 12 and the number of the male clasps 35 is four (4), so as to ensure the reliability of connection and make full use of a space on the eyeshade main body 10 and a space on the controller 30.

Figure 4:
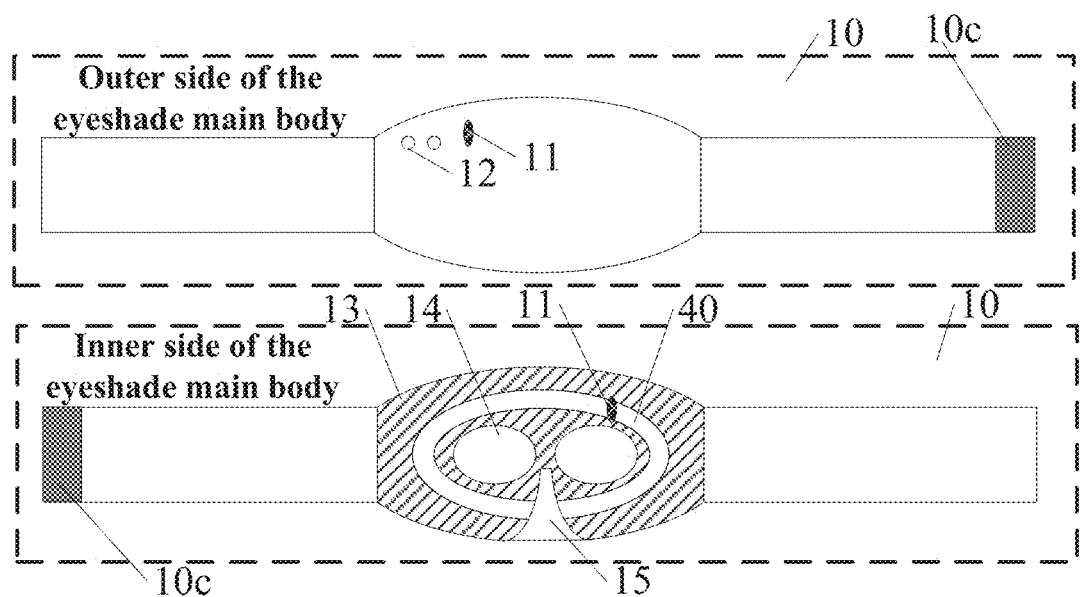
FIG. 4 is a schematic structural diagram of an eyeshade main body according to an embodiment of the present disclosure.

FIG. 4 is a schematic structural diagram of an eyeshade main body according to an embodiment of the present disclosure. As shown in FIG. 4, a light-shielding layer 13 is disposed on the inner side of the eyeshade main body 10, and first recesses 14 (for example, two first recesses 14) are provided in a portion of the light-shielding layer 13 that overlaps with the eye region of the wearer when the eyeshade is worn by the wearer.

In some embodiments, the light-shielding layer 13 may fit the wearer's face, thereby completely shielding the light. Since the first recesses 14 are provided in the portion of the light-shielding layers 13 that overlap with the eye region of the wearer when the eyeshade is worn by the wearer, the light-shielding layer 13 does not press the wearer's eyeballs. In some embodiments, when a width of the eyeshade main body 10 (that is, a dimension in the top-to-bottom direction of FIG. 4) is relatively large, a second recess 15 may be provided in the light-shielding layer 13 so that the light-shielding layer 13 fits the wearer's nose when the eyeshade is worn by the wearer to prevent light leakage. In some embodiments, the opening 11 is located outside an area of the eyeshade main body 10 that overlaps with the eye region of the wearer when the eyeshade is worn by the wearer to prevent light leakage.

In some embodiments, the heating unit 40 is disposed within the light-shielding layer 13.

In some embodiments, the heating unit 40 includes a material of graphene.

In some embodiments, as shown in FIG. 1, the eyeshade main body 10 includes a first main body portion 10a and two second main body portions 10b respectively located on both sides of the first main body portion 10a. The opening 11, the controller 30, the light-shielding layer 13, and the heating unit 40 are disposed on the first main body portion 10a. One end of each of the second main body portions 10b is coupled to the first main body portion 10a, and the other ends of the two second main body portions 10b may be coupled with each other through the adhesive unit 1c when the eyeshade main body 10 is wrapped around the head of the wearer (that is, the wearer wears the eyeshade). The first and second main body portions 10a, 10b may have relatively large widths so as to disperse pressure from the eyeshade to different locations of the head of the wearer to avoid discomfort of the wearer caused by excessive local pressure.

In some embodiments, the controller 30 further includes a power interface. The power interface is coupled to a power source (for example, a battery or an AC power source) when the eyeshade is worn by the wearer, so as to supply power to the eyeshade.

An embodiment of the present disclosure further provides an electroencephalogram detection system including the eyeshade described above and an upper computer, and the upper computer is configured to receive the communication signal transmitted from the converter 31 and to evaluate the degree(s) of relaxation and/or tension of the brain of the wearer according to the communication signal.

The electroencephalogram detection system according to the embodiment of the present disclosure includes the heating unit 40 and the electroencephalogram acquisition unit 20, and thus the eyeshade can acquire the brain electrical signal of the wearer while heating the eye region of the wearer. In some embodiments, the electroencephalogram acquisition unit 20 is detachable, so that the wearer can detach the electroencephalogram acquisition unit 20 from the eyeshade when the brain electrical signal is not acquired to reduce the weight of the eyeshade.

It will be understood that the above embodiments are merely exemplary embodiments to explain the principle of the present disclosure, and the present disclosure is not limited thereto. It will be apparent to one of ordinary skill in the art that various changes and modifications can be made therein without departing from the spirit and scope of the disclosure, and these changes and modifications are to be considered within the scope of the disclosure.

What is claimed is:

1. An eyeshade, comprising:
   an eyeshade main body; and
   an electroencephalogram acquisition unit, a controller and a heating unit which are disposed on the eyeshade main body,
   wherein the electroencephalogram acquisition unit is configured to acquire a brain electrical signal of a wearer;
   the controller comprises a converter and is configured to receive the brain electrical signal from the electroencephalogram acquisition unit, the converter is detachably coupled to the electroencephalogram acquisition unit and is configured to convert the brain electrical signal into a communication signal and transmit the communication signal to an outside of the eyeshade while being coupled to the electroencephalogram acquisition unit; and
   the heating unit is configured to heat an eye region of the wearer, wherein the heating unit comprises a material of graphene;
   wherein the controller further comprises a first coupling structure which is electrically conductive, the electroencephalogram acquisition unit comprises a second coupling structure which is electrically conductive, and the electroencephalogram acquisition unit is detachably coupled to the first coupling structure of the controller by the second coupling structure; and
   while the second coupling structure is coupled to the first coupling structure, the electroencephalogram acquisition unit is electrically coupled to the converter, and the brain electrical signal is transmitted from the electroencephalogram acquisition unit to the converter;
   wherein the first coupling structure comprises a data interface and the second coupling structure comprises a data interface that matches with the data interface of the first coupling structure, the electroencephalogram acquisition unit is detachably coupled to the controller through the data interface of the first coupling structure and the data interface of the second coupling structure, and the controller receives the brain electrical signal from the second coupling structure through the data interface of the first coupling structure.

2. The eyeshade of claim 1, wherein the controller further comprises a temperature controller coupled to the heating unit and configured to adjust a heating temperature of the heating unit.

3. The eyeshade of claim 2, wherein the wearer provides a control instruction to the temperature controller, and the temperature controller adjusts the heating temperature of the heating unit according to the control instruction.

4. The eyeshade of claim 2, wherein the controller further comprises a processor, the processor is coupled to the temperature controller and the electroencephalogram acquisition unit and configured to generate a control signal according to the brain electrical signal acquired by the electroencephalogram acquisition unit, and the temperature controller is configured to adjust the heating temperature of the heating unit according to the control signal.

5. The eyeshade of claim 2, wherein a fixing member which is electrically conductive is disposed on an outer side of the eyeshade main body, the controller is fixed to the eyeshade main body through the fixing member, and the temperature controller is electrically coupled to the heating unit through the fixing member.

6. The eyeshade of claim 5, wherein the fixing member comprises a magnetic clasp.

7. The eyeshade of claim 1, wherein the converter comprises an analog-to-digital conversion circuit which converts the brain electrical signal being an analog signal into a digital brain electrical signal, and a wireless transmission circuit which transmits the digital brain electrical signal to an upper computer.

8. The eyeshade of claim 7, wherein the analog-to-digital conversion circuit comprises an analog-to-digital converter, and the wireless transmission circuit comprises a bluetooth module, a Wi-Fi module, or a Zigbee module.

9. The eyeshade of claim 1, wherein the electroencephalogram acquisition unit comprises a flexible circuit board and an electrode disposed on the flexible circuit board; and
   the controller is disposed on an outer side of the eyeshade main body, an opening is provided in a portion of the eyeshade main body that overlaps with a forehead of the wearer while the eyeshade is worn by the wearer, the flexible circuit board is detachably coupled to the controller, and the flexible circuit board is configured for passing through the opening.

10. The eyeshade of claim 9, wherein the electrode comprises a plurality of sub-electrodes comprising differential electrodes and a reference electrode; and
    a differential signal receiving port of the controller is configured to receive a signal acquired by the differential electrodes, and a reference voltage receiving port of the controller is configured to receive a signal acquired by the reference electrode.

11. The eyeshade of claim 10, wherein the differential electrodes and the reference electrode are arranged in a direction parallel to a length of the flexible circuit board, and the differential electrodes comprise first and second differential electrodes respectively located on both sides of the reference electrode.

12. The eyeshade of claim 9, wherein an adhesive unit is provided on a side of the flexible circuit board distal to the electrodes and/or on both ends of the eyeshade main body.

13. The eyeshade of claim 1, wherein a light-shielding layer is disposed on an inner side of the eyeshade main body, and recesses are provided in a portion of the light-shielding layer that overlaps with the eye region of the wearer while the eyeshade is worn by the wearer.

14. The eyeshade of claim 13, wherein the heating unit is disposed within the light-shielding layer.

15. The eyeshade of claim 1, wherein the controller is in wireless communication with the electroencephalogram acquisition unit.

16. The eyeshade of claim 1, wherein the heating unit is disposed on an inner side of the eyeshade main body and overlaps with the eye region of the wearer while the eyeshade is worn by the wearer.

17. An electroencephalogram detection system, comprising the eyeshade of claim 1 and an upper computer, wherein the upper computer is configured to receive the communication signal transmitted from the converter and to evaluate a degree of relaxation or tension of the brain of the wearer according to the communication signal.

* * * * *